United States Patent [19]

Watanabe et al.

[11] Patent Number: 4,562,154

[45] Date of Patent: Dec. 31, 1985

[54] CONTINUOUS ALCOHOL MANUFACTURING PROCESS USING YEAST

[75] Inventors: Keiichiro Watanabe; Tomiaki Yamada, both of Yokohama; Tsuneo Sazanami, Yokosuka; Eiko Asahara, Kiyose, all of Japan

[73] Assignees: JGC Corporation, Tokyo; Kansai Paint Co., Ltd., Amagasaki, both of Japan

[21] Appl. No.: 522,545

[22] Filed: Aug. 11, 1983

Related U.S. Application Data

[63] Continuation of Ser. No. 266,866, May 26, 1981, abandoned.

[30] Foreign Application Priority Data

May 28, 1980 [JP] Japan ................................. 55-70943

[51] Int. Cl.4 ............................................... C12P 7/14
[52] U.S. Cl. .................................... 435/162; 435/813; 435/911; 435/942
[58] Field of Search ................. 435/161, 162, 813, 42, 435/174, 178, 180, 244

[56] References Cited

U.S. PATENT DOCUMENTS 2,371,208  3/1945  Alzola ................................ 435/162
4,127,447 11/1978  Griffith et al. ...................... 435/162
4,242,454 12/1980  Muller et al. ....................... 435/162
4,310,629  1/1982  Muller et al. ....................... 435/162
4,315,987  2/1982  Muller et al. ....................... 435/162

Primary Examiner—R. B. Penland
Attorney, Agent, or Firm—Flynn, Thiel, Boutell & Tanis

[57] ABSTRACT

A continuous alcohol manufacturing process using yeast comprising a zone where a conventional yeast (Yeast B) which has an alcohol producing activity is mainly present (zone of Yeast B); a zone disposed in the fore part of said zone of Yeast B where a yeast (Yeast A) which has an alcohol producing activity and is superior in sugar resistance as compared with Yeast B is mainly present (zone of Yeast A); and a zone disposed in the rear part of said zone of Yeast B where a yeast (Yeast C) which has an alcohol has an alcohol producing activity and is superior in alcohol resistance as compared with Yeast B is mainly present (zone of Yeast C), wherein a substrate solution is supplied to said zone of Yeast A thereby to effect alcohol fermentation; the resulting fermentation liquid is introduced in said zone of Yeast B thereby to effect alcohol fermentation; the resulting fermentation liquid is further introduced in said zone of Yeast C thereby to effect alcohol fermentation; and then a product alcohol broth is obtained from said zone of Yeast C.

5 Claims, No Drawings

CONTINUOUS ALCOHOL MANUFACTURING PROCESS USING YEAST

This application is a continuation of U.S. Ser. No. 266,866, filed May 26, 1981, now abandoned.

BACKGROUND OF THE INVENTION (a) Field of the invention

The present invention relates to a continuous alcohol manufacturing process using yeast, in particular an alcohol manufacturing process which is designed to effect continuous alcohol fermentation by making three kinds of yeasts having an alcohol producing activity respectively (three kinds of alcohol fermentation yeasts) be present individually in series and introducing a substrate solution in each of them.

(b) Description of the prior art

Alcohol (ethyl alcohol) is widely used for not only drinking but also various industrial purposes, and is manufactured by the fermentation method and the synthesis method. In the manufacture of alcohol on an industrial scale according to the fermentation method, where molasses is used as the starting material, part of said molasses is first diluted with hot water to such an extent that its total sugar content becomes about 15 wt./V%, then a nutrient is added thereto for pH adjusting purposes, and the same is sterilized. After completion of said sterilization, the same is cooled to about 30° C., and then is inoculated with yeast fungus and cultured for about 2 days to prepare a seed culture (seed yeast). On the other hand, the remainder of said molasses is diluted with hot water to such an extent that its total sugar content becomes about 25 wt./V%, then the aforesaid seed yeast is added thereto, and thus fermentation is conducted at about 30° C. The fermentation is completed in about 4 days and a broth containing about 13 vol% alcohol is prepared. Successively, the yeast is removed from the obtained alcohol broth, and the latter is distilled to obtain alcohol (ethyl alcohol).

However, the fact is that the aforesaid manufacture of alcohol according to the fermentation method is conducted in a batch culture, and that said batch culture includes drawbacks or disadvantages to be solved, for instance, (1) since the yeast concentration is in a low range such as 3-4 g/l, a large capacity fermentor is needed in order to produce alcohol in a desired amount, (2) since the reaction speed is slow, the fermentation time is prolonged and consequently the productivity is deteriorated, and (3) since the alcohol and the other by-products strongly retard the reaction speed, the concentration of product alcohol must naturally be reduced from the viewpoint of manufacturing alcohol economically, and the like.

In order to solve these problems and profitably carry out the manufacture of alcohol according to the fermentation method, as a matter of course there have been proposed various procedures, for instance, to conduct the manufacture of alcohol continuously while dispersing yeast in a substrate solution, to prepare an immobilized yeast by immobilizing a living yeast on a carrier and utilize this (immobilized yeast) in a living or growing state and so forth.

The alcohol fermentation method using this immobilized yeast has been proposed very recently. For instance, a continuous alcohol manufacturing method is disclosed which comprises supplying a glucose-containing nutritional medium to an immobilized yeast obtained by immobilizing a concentrated yeast (Saccharomyces carbergensis) with carrageenan or a concentrated yeast (Saccharomyces cerevisiae) with polyacrylamide [which see "Kagaku Kozyo" (Chemical Factories) vol. 23, No. 3, pp.26–30 (published by Nikkan Kogyo Shinbun Sha)].

The continuous culture to be practiced without immobilizing yeast as above mentioned (namely, while dispersing yeast in a substrate solution) and the continuous culture using immobilized yeast may be expected to be more profitable than the conventional batch culture in that alcohol can be manufactured in a relatively short time and consequently the fermentor can achieve a high volumetric efficiency (alcohol productivity of fermentor per unit volume and unit time). On the other hand, however, there is no denying the fact that when the conventional yeast that has generally been used in alcohol fermentation is employed, even these continuous cultures must also reduce the concentration of the fermentation product alcohol as in the case of batch culture because said yeast is subject to retardments caused by the osmotic pressure of a substrate (sugar) and the product (alcohol).

In this connection, it is to be noted that the conventional yeast that has normally been used in alcohol fermentation can not endure a sugar concentration up to about 25 wt./V% at most, although this concentration is variable depending on the kind of yeast. When said concentration is in excess of this limit, the osmotic pressure of the substrate is so elevated that the activity of the yeast is reduced or restricted to an extreme degree. Further, in view of the fact that yeast loses its activity owing to the retarding action of the alcohol when the alcohol concentration is high, there is no possibility of expecting the manufacture of a broth having a high alcohol concentration. To cope with this, it is sometimes adopted to supply a batch of substrate solution (sugar solution) even in the case of batch system fermentation or to take a long period of time for fermentation, although variable depending on the kind of yeast, when there is a necessity of obtaining a broth of high alcohol concentration (alcohol concentration of about 18 vol.%), but these procedures are unprofitable.

It is found that the object of manufacturing alcohol economically as well as effectively can be achieved by obtaining a broth having an alcohol concentration upto about 13 vol./%. Accordingly, the fact is that the broth having the aforesaid alcohol concentration is now being manufactured.

SUMMARY OF THE INVENTION

In the light of the present condition as above mentioned, the inventors have carried out a series of investigations and discovered that a highly concentrated alcohol broth can be obtained effectively by using a specific combination of a previously used conventional yeast which has an alcohol producing activity, with a yeast which has an alcohol producing activity and is superior in sugar resistance to the conventional yeast, and a yeast which has an alcohol producing activity and is superior in alcohol resistance to the conventional yeast. The present invention has been completed on the basis of this discovery.

Accordingly, the object of the present invention is to provide a continuous alcohol manufacturing process using yeast which can eliminate the aforesaid drawbacks inherent in conventional methods and can obtain a highly concentrated alcohol broth effectively.

In particular, the continuous alcohol manufacturing process using yeast according to the present invention may be said to comprise the provision of a zone where a conventional yeast having an alcohol producing activity (which will be referred to as Yeast B hereinafter) is mainly present (zone of Yeast B), a zone disposed before said zone of Yeast B wherein a yeast which has an alcohol producing activity and is superior in sugar resistance as compared with Yeast B (which will be referred to as Yeast A hereinafter) is mainly present (zone of Yeast A); and a zone disposed following said zone of Yeast B wherein a yeast which has an alcohol producing activity and is superior in alcohol resistance as compared with Yeast B (which will be referred to as Yeast C hereinafter) is mainly present (zone of Yeast C) and is characterized in that a product alcohol broth can be obtained from the zone of Yeast C through the following steps of:

(1) supply a substrate solution to the zone of Yeast A to thereby effect alcohol fermentation;
(2) introducing, in the zone of Yeast B, only the fermentation liquid derived from the zone of Yeast A or substrate solution in an amount smaller than that of the substrate solution supplied to the zone of Yeast A together with the fermentation liquid derived from the zone of Yeast A to thereby effect alcohol fermentation; and then
(3) introducing, in the zone of Yeast C, only the fermentation liquid derived from the zone of Yeast B or a substrate solution in an amount smaller than that of the substrate solution supplied to the zone of Yeast A together with the fermentation liquid derived from the zone of Yeast B to thereby effect alcohol fermentation, whereby a product alcohol broth is derived from the zone of Yeast C.

DETAILED DESCRIPTION OF THE PREFERRED EMBODIMENTS OF THE INVENTION

The process of the present invention employs three kinds of yeasts having a different performance (property) respectively that is, a conventional yeast (Yeast B) having an alcohol producing activity, a yeast (Yeast A) which has an alcohol producing activity and is superior in sugar resistance as compared with Yeast B and a yeast (Yeast C), which has an alcohol producing activity and is superior in alcohol resistance as compared with Yeast B. The yeast referred to as Yeast B herein is one which has generally been used also in the alcohol fermentation field and is capable of achieving a normal alcohol fermentation under the conditions: the sugar concentration of a substrate solution used is about 23-27 wt./V% or less and the alcohol concentration is up to about 15-17 vol. % though variable depending on the kind of yeast.

Yeast A is one which is capable of achieving alcohol fermentation at a sugar concentration higher than that of Yeast B, and Yeast C is one which is capable of achieving alcohol fermentation at an alcohol concentration higher than that of Yeast B.

As typical examples of Yeast A there can be enumerated Saccharomyces rouxii, Zygosaccharomyces japonicus, Zygosaccharomyces majar and Zygosaccharomyces soya.

As typical examples of Yeast B there can be enumerated Saccharomyces cerevisiae, Saccharomyces formosensis, Saccharomyces robustus and Saccharomyces carlsbergensis.

As typical examples of Yeast C there can be enumerated Schizosaccharomyces pombo, Schizosaccharomyces octosporus, Schizosaccharomyces mellacei and alcohol resistant yeasts manufactured by Nihon Zyozo Kyokai.

In the application of these yeasts to the manufacture of alcohol, where yeasts are of course used in a living state, the following modes are contemplated, such as (I) to use yeast in a state suspended in a substrate solution and (II) to use yeast in a state immobilized on a carrier so that the yeast may repeat its growth.

In the above (I), it will suffice if the yeast per se is allowed to exist directly in a substrate solution. And, in the above (II), it will suffice if a substrate solution is allowed to contact with immobilized yeast prepared by entrapping and immobilizing a yeast on a carrier or by adhering yeast onto a carrier. The method for preparing immobilized yeast per se is well known. Reciting one example thereof, an intended immobilized yeast can be obtained by thermally dissolving a fixed amount of a carrier such as carrageenan, agar or the like in water; cooling the resulting solution to obtain an aqueous solution; mingling a fixed amount of yeast with said aqueous solution; further cooling this mixture for gelation; and then forming the resulting gel into a desired shape.

In case where collagen is employed as a carrier, an intended immobilized yeast may be obtained by the steps of swelling and solubilizing, for instance, oxhide powder, with an alkaline amine solution; mingling the same with yeast; spreading the resulting mixed solution onto a flat plate for air drying purposes; and thereafter treating the same with glutaraldehyde to thereby from it into a desired shape. Furthermore, in case where polyacrylamide is used as a carrier, an intended immobilized yeast may be obtained by the steps of adding, to a fixed amount of yeast-containing solution, acrylamide monomer, crosslinking agent (for instance, N,N'-methylenebisacrylamide), polymerization promotor (for instance, dimethylaminopropionitrile) and polymerization initiator (for instance, potassium persulfate) for polymerizing purposes; then cooling this for gelation; and thereafter forming the resulting gel into a desired shape.

The immobilized yeast suitably used in the process of the present invention includes one prepared by immobilizing yeast on a carrier by virtue of irradiation of radioactive rays besides those enumerated above. For instance, this can be obtained by of mingling a fixed amount of yeast with an aqueous polyvinyl alcohol solution; pouring this mixed solution into an ampoule; subjecting the same to irradiation of radioactive rays for gelation; and then forming the resulting gel into a desired shape. The immobilized yeast may also be obtained by mingling a photo-crosslinked resin with an aqueous yeast suspension; subjecting the resulting mixture to irradiation of actinic rays; and forming the resulting immobilized matter into a desired shape. The shape of the immobilized yeast may be any one of globular, prismatic, columnar, ring and filmy shapes.

According to the process of the present invention, alcohol fermentation is completed by of effecting the fermentation reaction by using Yeast A at a high sugar concentration stage in which Yeast B would be liable to retardment by the osmotic pressure resulting from the sugar concentration of a substrate; further effecting the fermentation reaction by using Yeast B at a stage where the sugar concentration is reduced to such an extent as Yeast B is freed from said retardment; and successively promoting the fermentation reaction by using Yeast C at a stage where the alcohol concentration has further increased so that conspicuous retardment of yeast B would be caused by alcohol.

Accordingly, when these yeasts are applied to the alcohol fermentation reaction in the form of immobilized yeast, the immobilized yeast is arranged so that (1) the packing zones for the respective immobilized yeasts—Yeast A, Yeast B and Yeast C—are defined in one column (fermentation device) by means of for instance partition plates or (2) these three kinds of immobilized yeasts are packed in their own separate fermentation devices, and then a substrate solution is introduced in the packing zone (or fermentation device) of Yeast A and the alcohol fermentation liquid obtained in this packing zone (or fermentation device) is allowed to successively pass through the packing zone (or fermentation device) of Yeast B and then the packing zone (or fermentation device) of Yeast C. Continuous supply of the substrate solution results in that a product alcohol broth can be continuously withdrawn from the packing zone (or fermentation device) of Yeast C.

In case where the alcohol fermentation is carried out without using immobilized yeasts, namely while dispersing them in a substrate solution, the yeasts are arranged as in the case of using the aforesaid immobilized yeasts, that is, (1') the zones where the respective yeasts are mainly present may be defined in one fermentation device (wherein, a means is provided to prevent the occurrence of liquid mixing between mutual zones) or (2') the zones where the respective yeasts are mainly present may be installed separately from each other. And, in this instance, first each yeast is batchcultured in each zone, and then when the concentration of each yeast has been held in stationary state, a substrate solution is allowed to pass through the zone (or fermentation device) of Yeast A, the zone (or fermentation device) of Yeast B and the Zone (or fermentation device) of Yeast C in that order.

At the time of utilizing these yeasts in suspending the suspended state, however, it is necessary to properly set the residence time of substrate solution (or alcohol fermentation liquid) in the zone of each yeast lest the so-called "wash-out phenomenon of yeast" should take place, said phenomenon arising for the reason that the growth speed of yeast in each zone can not follow the dilution speed of yeast according to the effluence of liquid from its zone.

In practicing the process of the present invention, it is required that the dimension, construction and the like of the zone of each yeast should be determined properly taking into consideration the factors of each yeast such as the alcohol fermentation speed, degree of retardment caused by the osmotic pressure resulting from the sugar concentration of the substrate, degree of retardment caused by alcohol and the like, irrespective of whether the yeast used herein is immobilized on a carrier or suspended in a substrate solution.

In this connection, it is to be noted that according to the process of the present invention fit is permitted to adopt the above mentioned method wherein the substrate solution is supplied to the zone of Yeast A alone and thence is allowed to pass through the zone of Yeast B and the zone of Yeast C in succession, whereby a highly concentrated product alcohol broth is obtained, and moreover another method which comprises not only supplying the substrate solution to the zone of Yeast A but also introducing, in the zone of Yeast B and the zone of Yeast C, the substrate solution in amounts smaller than that supplied to the zone of Yeast A.

The devices used for forming the zones of yeast in the present invention may include a suspension vessel used for the yeast in the suspended state, and on the other hand may include a stirring vessel and a reaction means having a charging layer, a transfer layer or a fluid layer besides a suspending layer in the case of using the yeast in the immobilized state. These means may be properly selected in accordance with the dimension, configuration and the like of the immobilized yeast.

The fermentation conditions are the same as those for normal alcohol fermentation, that is, the suitable fermentation temperature is about 30° C. and the suitable pH value is in the range of about 4.0–5.0. As the starting material there can be used any sugar solution containing nutritional salts. Typically there can be enumerated grape sugar solution, cane molasses solution, refined sugar, beet molasses solution, blackstrap molasses solution and the like.

As is seen from the aforegoing, the process according to the present invention is designed to manufacture a highly concentrated alcohol broth through the steps of arranging three kinds of yeasts in series and effecting fermentation reactions in succession. The broth obtained by means of the present manufacturing process is then introduced into a separation-refining step where it is refined by separating the normal yeast and the like contained therein and distilling to obtain a product alcohol. According to the present process as mentioned above, there can be obtained a highly concentrated alcohol of about 20 vol.% more easily than conventional alcohol fermentation methods. In addition, the process of the present invention is advantageous in that a continuous alcohol manufacturing operation can be carried out effectively due to the fact that even when the alcohol concentration of the fermentation liquid is elevated to a considerable degree the activity of the yeast is not deteriorated easily.

EXAMPLES

EXAMPLE 1

Zygosaccharomyces majar as a sugar resistance yeast, Saccharomyces cerevisiae as a conventional alcohol producing activity yeast and Schizosaccharomyces mellacei as an alcohol resistant yeast were each subjected to shake culture treatment in its own molasses medium (the sugar concentration of which is about 20 wt./V%) and thus grown to thereby obtain each yeast liquid.

Fermentors (A), (B) and (C) were prepared by charging a jar fermentor of net volume 3 l (MB-C Type manufactured by Iwashiya K.K.) with a molasses medium in amounts of 1.3 l, 1.05 l and 0.9 l respectively. Then, the aforesaid sugar resistant yeast liquid was poured into fermentor (A), conventional alcohol producing activity yeast liquid into fermentor (B) and alcohol resistance yeast liquid into fermentor (C) respectively for regulating the initial yeast concentration to $1-2 \times 10^7$ (the number of yeast)/ml (0.2–0.4 g/l). And, these yeasts were subjected to batch system fermentation under the conditions: the draft amount, 1 l/hr and the number of stirring, 250 r.p.m.

The yeast concentration in each fermentator became $2-3 \times 10^8$ (the number of yeast)/ml (4–6 g/l) after the lapse of 18–23 hours, and the alcohol produced at this time in fermentors (A), (B) and (C) was about 6.3 vol.% about 9.5 vol.% and about 7.6 vol.% respectively.

At this stage, the operation was changed over to continuous fermentation by beginning to continuously supply a molasses medium having a sugar concentration of about 35 wt./V% into the fermentor charged with sugar-resistant yeast (fermentor A) and on the other hand withdrawing the same amount from said fermentor. Then, a continuous fermentation operation was carried out by using fermentors arranged in series in such a manner that the liquid derived from fermentor A was supplied to the fermentor charged with conventional alcohol producing activity yeast (fermentor B), the same amount of liquid was derived from fermentor B and supplied to the fermentor charged with alcohol resistance yeast (fermentor C), and the same amount of liquid was derived from fermentor C. Said continuous fermentation was carried out under the conditions: the draft amount, 0.5 l/hr and the number of stirring, 250 r.p.m. This three-stage continuous fermentation operation using fermentors arranged in series became stable after the lapse of about 200 hours, and about 18 vol.% of alcohol were produced continuously for 350 hours or more. In this instance, the residence times of liquid in fermentors A, B and C were 26 hours, 21 hours, and 18 hours respectively.

EXAMPLE 2

Zygosaccharomyces majar as a sugar resistant yeast, Saccharomyces cerevisiae as a conventional alcohol producing activity yeast and Schizosaccharomyces mellacei as an alcohol resistant yeast were each subjected to shake culture treatment in its own molassed medium (the sugar concentration of which was about 20 wt./V%). After the growth of yeasts had been confirmed, said yeasts were recovered by means of a centrifugal separator and thus their suspensions were obtained.

To 50 ml of the suspension of each yeast were added 9.4 g of acrylamide monomer and 0.5 g of N'-methylenebisacrylamide and further added 5 ml of a 5% dimethylaminopropionitrile as a polymerization promotor and 5 ml of a 2.5% potassium persulfate as a polymerization initiator. This mixture was well mingled and poured in a 25 cm long and 25 cm broad frame defined with 1 mm-thick spacers on a polypropylene film (50 $\mu$ thick) spread on a glass plate. The same was maintained at a low temperature (10° C.) and gelation thereof was completed for about 15 minutes, whereby a sheet of each immobilized yeast (about 1 mm thick) was obtained. In this instance, this immobilized yeast in dry state was found to have a yeast concentration of 5 wt.% relative to the total weight thereof. The thus obtained sheet-like immobilized yeast was further cut into about 1 mm×1 mm pieces. These are called samples of each immobilized yeast hereinafter. 45 ml of the thus obtained samples of the sugar resistance immobilized yeast were charged in a 20 mm across and 360 mm high column (which is called column A), 50 ml of samples of the conventional alcohol producing activity immobilized yeast were charged in a 20 mm across and 400 mm high column (which is called column B), and 55 ml of the alcohol resistant immobilized yeast were charged in a 20 mm across and 400 mm high column (which is called column C).

An ammonium salt-containing molasses medium, the sugar concentration thereof being about 35.5 wt./V/%, was supplied successively to columns A, B and C so that the contact time might be 8.5 hours, 9.5 hours and 10.5 hours respectively to thereby effect a continuous alcohol fermentation. As a result, 18–20 vol.% of ethanol were produced continuously for 3000 hours or more. In this instance, it was found that the liquid introduced into column B had a sugar concentration of 25–26 wt./V% and the liquid derived from column B had an alcohol concentration of 16–17 vol.%. And, the reaction temperature in this instance was 30°–32° C. and the pH was 4.5–5.0.

EXAMPLE 3

Saccharomyces rouxii as a sugar resistant yeast, Saccharomyces formosensis NaKaZaWa as a conventional alcohol producing activity yeast and Schizo Saccharomyces pombo as an alcohol resistant yeast were each subjected to shake culture treatment in its own molasses medium (the sugar concentration of which was about 20 wt./V%). After the growth of yeasts had been confirmed, said yeasts were recovered by means of a centrifugal separator and their suspensions were obtained. A urethanated prepolymer (average molecular weight: about 5000) comprising 2000 g of polyethylene glycol (average molecular weight: about 4000), 1 mol (222 g) of isophoronediisocyanate and 1 mol (130 g) of 2-hydroxyethyl methacrylate was suspended in distilled water so as to become 65% by weight. 50 parts by weight of this suspension were derived. To this were added 0.5 part by weight of a photosensitizer, i.e., benzoinethyl ether and 60 parts by weight of aforesaid yeast suspension. This mixture was dispersed uniformly by means of a homogenizer. The resulting dispersion was poured in a 10 cm long and 10 cm broad frame defined with 1 mm-thick spacers on a polypropylene film (50 $\mu$ thick) spread on a glass plate, and the same was covered with a polypropylene film (50$\mu$ thick) to prevent the air from entering thereinto. This was subjected to 3–6 minutes' irradiation of light from low pressure mercury lamps (3600 Å) disposed 5 cm above and below the glass plate, and thereafter the polypropylene film was peeled off, thereby obtaining an about 1 mm-thick filmy immobilized yeast. Each of the thus obtained immobilized yeasts in dry state was found to have a yeast concentration of 5% by weight relative to the total weight of the immobilized yeast. Each of these filmy immobilized yeasts was further cut into sheet-like ones. The dimensions of this sheet-like one is about 1 mm thick×50 mm broad×100 mm long.

In the case of each yeast, 19 sheets of said sheet-like immobilized yeast were charged in a reactor unit whose dimensions is 50 mm long×50 mm broad×100 mm high by the aid of spacers so that the distance between the sheets may be 1.55 mm, whereby there was prepared a reactor unit for use in each yeast. The immobilized yeast sheets charged in the units were arranged to extend parallel with the flow of the substrate solution and the number of units used was adjusted depending on the kind of yeast, whereby there was prepared a reactor including the charging zone of each yeast (three kinds) wherein a plurality of units were charged in multistage manner.

An ammonium salt-containing molasses medium, the sugar concentration thereof being about 35.5 wt./V%, was supplied to a charging zone A of sheet-like immobilized surgar resistant yeast disposed within the reactor and was kept in contact for 7.5 hours to thereby attain alcohol fermentation. And, a continuous alcohol fermentation was carried out in the manner of allowing the liquid obtained herein to flow next into a charging zone B of sheet-like immobilized conventional alcohol producing activity yeast and further in a charging zone C of sheet-like immobilized alcohol resistant yeast. The contact time of liquid in each of the charging zones B and C was 8.5 hours and 9.5 hours respectively. And, the reaction temperature and pH were set to the same values of Example 2. As a result, it became possible to manufacture 19–20 vol.% of ethanol continuously for 4000 hours or more.

EXAMPLE 4

The same three kinds of yeast as in Example 3 were immobilized according to the same procedure as Example 3 to thereby obtain the respective film immobilized yeasts having a thickness of about 1 mm. These filmy immobilized yeasts were further cut into 1 mm thick×1 mm long×1 mm broad samples, thereby obtaining the respective kinds of immobilized yeasts, i.e., sugar resistant immobilized yeast, conventional alcohol producing activity immobilized yeast and alcohol resistant immobilized yeast. In this instance, each immobilized yeast in the dry state was found to have a yeast concentration of 5% by weight relative to the total weight thereof.

Next, 33 ml of sugar resistant immobilized yeast samples were charged in a 20 mm across and 265 mm high column (which is called column A), 50 ml of conventional alcohol producing activity immobilized samples were charged in a 20 mm across and 400 mm high column (which is called column B), and 42 ml of alcohol resistant immobilized yeast samples were charged in a 20 mm across and 340 mm high column (which is called column C).

An ammonium salt-containing molasses medium, the sugar concentration thereof being about 32 wt./V%, was supplied to column A so that the contact time might be 7.5 hours, thereby effecting a alcohol fermentation reaction. To the liquid derived from this column A there was continuously supplied a molasses medium which contains ammonium salt in a liquid volume of 1/5 relative to the derived liquid and has a sugar concentration of about 45 wt./V%. Then, this mixed solution was allowed to pass through column B and column C in succession and a continuous alcohol fermentation was thus carried out. The contact time of liquid with column B and column C in this instance was found to be 9.5 hours and 8 hours respectively.

Consequently, 18.5–19.5 vol.% of ethanol was produced continuously for 1000 liquid hours or more. In this instance, the mixed solution introduced into column B was found to have a sugar concentration of about 26 wt./V% and the solution derived from column B was found to have an alcohol concentration of about 16 vol.%. And, the reaction temperature and pH were set to have the same values as Example 2.

What is claimed is:

1. A continuous fermentation process for producing ethanol, which consists essentially of: introducing a stream of a fermentable sugar-containing feed liquor containing at least 23–27 wt./V% of sugar into a first fermentation zone containing viable yeast cells consisting essentially of cells of Yeast A immobilized on a photocross-linked resin carrier, and carrying out a first fermentation of said feed liquor to partially convert the sugar therein to ethanol and to produce a first effluent liquor containing ethanol and sugar, said Yeast A being capable of rapidly fermenting sugar contained in said feed liquor to produce ethanol and being superior in sugar resistance relative to a Yeast B so that Yeast A can ferment the sugar in said liquor when said liquor contains more than about 23–27 wt./V% of sugar, and said Yeast A being selected from the group consisting of *Saccharomyces rouxii, Zygosaccharomyces japonicus, Zygosaccharomyces majar* and *Zygosaccharomyces soya;* introducing a stream containing said first effluent liquor into a second fermentation zone containing viable yeast cells consisting essentially of cells of Yeast B immobilized on a photocross-linked resin carrier, and carrying out a second fermentation of said first effluent liquor to convert a further quantity of the sugar contained therein to ethanol and to produce a second effluent liquor containing ethanol and sugar, said Yeast B being inferior in sugar resistance relative to Yeast A and being capable of rapidly fermenting sugar contained in a fermentable sugar-containing liquor to produce ethanol under the conditions that said liquor contains up to about 23–27 wt./V% of sugar and up to about 15–17 vol.% of ethanol, said Yeast B being selected from the group consisting of *Saccharomyces cerevisiae, Saccharomyces formosensis, Saccharomyces robustus* and *Saccharomyces carlsbergensis;* introducing a stream containing said second effluent liquor into a third fermentation zone containing viable yeast cells consisting essentially of cells of Yeast C immobilized on a photocross-linked resin carrier, and carrying out a third fermentation of said second effluent liquor to convert an additional quantity of the sugar contained therein to ethanol, said Yeast C being capable of rapidly fermenting sugar contained in said second effluent liquor to produce ethanol and being superior in alcohol resistance relative to Yeast B so that Yeast C can ferment the sugar in said second effluent when said liquor contains more than about 15–17 vol.% of ethanol, and Yeast C being selected from the group consisting of *Schizosaccharomyces pombo, Schizosaccharomyces octosporus* and *Schizosaccharomyces mellacei;* and recovering an ethanol-containing broth containing at least about 18 vol.% of ethanol from said third fermentation zone.

2. A continuous fermentation process as claimed in claim 1 in which the stream introduced into at least one of said second and third fermentation zones includes the effluent liquor from the immediately preceding fermentation zone and a smaller quantity of a second fermentable sugar-containing liquor.

3. A continuous fermentation process as claimed in claim 1 in which said Yeast A is *Zygosaccharomyces majar,* said Yeast B is *Saccharomyces cerevisiae* and said Yeast C is *Schizosaccharomyces mellacei.*

4. A continuous fermentation process as claimed in claim 1 in which said Yeast A is *Saccharomyces rouxii,* said Yeast B is *Saccharomyces formosensis* and said Yeast C is *Schizosaccharomyces pombo.*

5. A continuous fermentation process as claimed in claim 1 in which said feed liquor contains more than 27 wt./V% sugar.

* * * * *